(12) United States Patent
Duan et al.

(10) Patent No.: US 12,178,197 B2
(45) Date of Patent: Dec. 31, 2024

(54) BREEDING AND AIR DRYING SYSTEM AND METHOD FOR SAPROPHAGOUS INSECT

(71) Applicant: ZHENGZHOU YAO'AN ENVIRONMENTAL PROTECTION TECHNOLOGY CO., LTD, Zhengzhou (CN)

(72) Inventors: Yonggai Duan, Sanmenxia (CN); Wei Chen, Zhumadian (CN); Yonghui He, Xinxiang (CN)

(73) Assignee: ZHENGZHOU YAO 'AN ENVIRONMENTAL PROTECTION TECHNOLOGY CO., LTD, Zhengzhou (CN)

( * ) Notice: Subject to any disclaimer, the term of this patent is extended or adjusted under 35 U.S.C. 154(b) by 0 days.

(21) Appl. No.: 18/291,581

(22) PCT Filed: Nov. 11, 2022

(86) PCT No.: PCT/CN2022/131266
§ 371 (c)(1),
(2) Date: Jan. 24, 2024

(87) PCT Pub. No.: WO2023/083278
PCT Pub. Date: May 19, 2023

(65) Prior Publication Data
US 2024/0260554 A1  Aug. 8, 2024

(30) Foreign Application Priority Data

Nov. 15, 2021 (CN) .......................... 202111347392.5

(51) Int. Cl.
*A01K 67/033* (2006.01)

(52) U.S. Cl.
CPC .................................. *A01K 67/033* (2013.01)

(58) Field of Classification Search
CPC ..................................................... A01K 67/033
See application file for complete search history.

(56) References Cited

U.S. PATENT DOCUMENTS 5,178,094 A * 1/1993 Carr ...................... A01K 67/033
119/6.5
6,342,499 B1 * 1/2002 Black ...................... A01K 51/00
514/579

(Continued)

FOREIGN PATENT DOCUMENTS

| CN | 103884159 A | 6/2014 |
| CN | 203709071 U | 7/2014 |

(Continued)

*Primary Examiner* — Monica L Perry
*Assistant Examiner* — Aaron M Rodziwicz
(74) *Attorney, Agent, or Firm* — Bayramoglu Law Offices LLC

(57) ABSTRACT

A breeding and air drying system and method for a saprophagous insect is configured to carry out breeding and air drying operations, and includes a breeding platform and an air drying system. The breeding platform includes a bottom sealing layer and a plurality of insect breeding layers. The insect breeding layer includes a breathable support plate and a baffle provided around the breathable support plate. The air drying system includes a drying air inlet provided below the breathable support plate. The drying air inlet is connected to an inlet of a hot air duct. The hot air duct is configured to provide dry hot air with an air drying effect.

17 Claims, 15 Drawing Sheets

(56) References Cited

U.S. PATENT DOCUMENTS

| | | | | |
|---|---|---|---|---|
| 6,474,259 | B1* | 11/2002 | Gaugler | A01K 67/033 |
| | | | | 119/6.7 |
| 9,629,339 | B2* | 4/2017 | Newton | A01K 5/00 |
| 10,362,772 | B2* | 7/2019 | Arsiwalla | A01K 67/033 |
| 2011/0139075 | A1* | 6/2011 | Shapiro Ilan | A01K 67/033 |
| | | | | 119/6.5 |
| 2012/0311926 | A1* | 12/2012 | Mittelmark | F24F 8/22 |
| | | | | 47/17 |
| 2015/0223496 | A1* | 8/2015 | Kitazumi | A01K 67/033 |
| | | | | 119/6.5 |
| 2015/0305320 | A1* | 10/2015 | Hedman | A01M 1/24 |
| | | | | 43/132.1 |
| 2022/0295766 | A1* | 9/2022 | Shih | A01K 67/033 |
| 2024/0092707 | A1* | 3/2024 | Caprio | B09B 3/60 |

FOREIGN PATENT DOCUMENTS

| | | | |
|---|---|---|---|
| CN | 206213054 | U | 6/2017 |
| CN | 206751634 | U | 12/2017 |
| CN | 210045537 | U | 2/2020 |
| CN | 210226597 | U | 4/2020 |
| CN | 112715486 | A | 4/2021 |
| CN | 213187729 | U | 5/2021 |
| CN | 113317283 | A | 8/2021 |
| CN | 115251011 | A | 11/2022 |
| JP | 2010110307 | A | 5/2010 |

* cited by examiner

BREEDING AND AIR DRYING SYSTEM AND METHOD FOR SAPROPHAGOUS INSECT

CROSS REFERENCE TO THE RELATED APPLICATIONS

This application is the national phase entry of International Application No. PCT/CN2022/131266, filed on Nov. 11, 2022, which is based upon and claims priority to Chinese Patent Application No. 202111347392.5, filed on Nov. 15, 2021, the entire contents of which are incorporated herein by reference.

TECHNICAL FIELD

The present disclosure relates to a breeding and air drying system and method for a saprophagous insect, and belongs to the field of insect breeding devices.

BACKGROUND

As a member of saprophagous stratiomyidae, *Hermetia illucens* L. can feed on organic waste such as poultry manure and meal waste, and produce high-value animal protein feed. *Hermetia illucens* L. can be utilized as resources due to their rapid reproduction, large biomass, wide range of food sources, high absorption and conversion rates, easy management, low breeding costs, and good animal palatability. In the prior art, the larvae of *Hermetia illucens* L. are fed on organic waste. Typically, the feed material has a moisture content of 60-80%, and after it is eaten by the larvae of *Hermetia illucens* L., the residue (mainly frass) has a moisture content of 45-65%, which does not meet the requirement of a national standard for the moisture content of organic fertilizers. The residue needs to be dried before use and storage. Typically, the existing drying method firstly separates the larvae and the frass through screening and then dries the frass by a drying device or high-temperature fermentation. The method has the following problems: (1) The frass has a high moisture content and high viscosity, making it difficult for screening. (2) A separate drying device is needed, resulting in high costs and too many steps. (3) The larvae are prone to death during the screening process, which reduces the yield of the larvae.

SUMMARY

To solve the technical problem, the present disclosure provides a breeding and air drying system and method for a saprophagous insect, which can simultaneously carry out insect breeding and air drying, effectively reducing the cost of *Hermetia illucens* L. breeding.

The present disclosure adopts the following technical solutions.

A breeding and air drying system for a saprophagous insect is configured to carry out breeding and air drying operations, and includes a breeding platform and an air drying system, where the breeding platform includes a bottom sealing layer and a plurality of insect breeding layers; the insect breeding layer includes a breathable support plate and a baffle provided around the breathable support plate; the air drying system includes a drying air inlet provided below the breathable support plate; the drying air inlet is connected to an inlet of a hot air duct; and the hot air duct is configured to provide dry hot air with an air drying effect.

Preferably, a top of the breeding platform is provided with an upper cover.

Preferably, the breeding and air drying system further includes a ventilation system; the ventilation system includes a breeding air inlet provided above or below the breathable support plate and an air outlet provided above the breathable support plate; the breeding air inlet is connected to a breeding air inlet duct; and the breeding air inlet duct is configured to provide a gas for controlling a temperature, a humidity, and an oxygen content of a breeding space.

Preferably, except for a top insect breeding layer, each of the insect breeding layers is provided with the breeding air inlet, the air outlet, and the drying air inlet; the breeding air inlet duct is provided with a breeding air inlet valve; an air outlet duct is provided with an air outlet valve; and the hot air duct is provided with a dry hot air inlet valve.

Preferably, the breeding and air drying system further includes a temperature and humidity sensor and a control system; and the breeding air inlet valve and the hot air inlet valve are electric valves, and the breeding air inlet valve and the hot air inlet valve are connected to the control system, respectively.

Preferably, the temperature and humidity sensor is provided at the air outlet.

Preferably, the insect breeding layer further includes a support fabric (or support mesh), a left roller, a right roller, and roller power mechanisms; the baffle includes a front baffle, a rear baffle, a left baffle, and a right baffle; the support fabric is in contact with the breathable support plate; two ends of the support fabric are respectively wound around the left roller and the right roller; the left roller and the right roller are fixed to a frame; the left roller and the right roller are respectively connected to the roller power mechanisms; the roller power mechanisms are respectively configured to drive the left roller and the right roller to rotate; the left baffle and/or the right baffle are movable structures that can be opened and closed; and when the left baffle and the right baffle are closed, the support fabric and the breathable support plate are tightly sealed.

Preferably, the roller power mechanism includes a linear guide rail, a guide rail motor, a roller motor, a driven gear provided at an end of the roller, and an driving gear provided at an end of the roller motor; the roller motor is fixed to a slider of the linear guide rail; and the guide rail motor drives the linear guide rail to move.

Preferably, the left baffle and/or the right baffle are fixed to the frame through a rotating shaft; and the rotating shaft is connected to a rotating shaft power mechanism.

Preferably, the insect breeding layer includes one end provided with an inert roller and the other end provided with a spreading roller and a larvae collection roller; the spreading roller is provided above the larvae collection roller; the spreading roller and the larvae collection roller are provided with a driving mechanism; the support fabric includes one end fixed to the spreading roller and the other end bypassing the inert roller, passing from an upper part of the breathable support plate, and fixed to the larvae collection roller; a length of the support fabric is three times a length of the insect breeding layer; and during breeding, the spreading roller is wound with one part of the support fabric with the same length as the insect breeding layer, and the remaining part of the support fabric is fixed between the spreading roller, the inert roller, and the larvae collection roller.

Preferably, the support fabric includes a plurality of pull ropes provided at two ends of the support fabric and having the same length as the insect breeding layer and a fabric belt provided at a middle; and a width of the fabric belt is the same as a width of the insect breeding layer.

Preferably, the insect breeding layer includes the breathable support plate and the baffle provided around the breathable support plate; the baffle includes the front baffle, the rear baffle, the left baffle, and the right baffle; the left baffle and/or the right baffle are respectively fixed to the frame through a rotating shaft; the rotating shaft is connected to a rotating shaft power mechanism; each of the front baffle and the rear baffle is provided in a sliding groove of the frame through a slider; each of the front baffle and the rear baffle includes an upper end provided with an upper elastic sealing mechanism and a lower end provided with a lower elastic sealing mechanism; an end of each of the front baffle and the rear baffle is connected to a sliding power mechanism; the upper elastic sealing mechanism is in contact with the breathable support plate of an upper insect breeding layer that is adjacent to and in contact with the insect breeding layer; the lower elastic sealing mechanism is in contact with the breathable support plate; the sliding power mechanism drives the front baffle and the rear baffle to move upwards to separate the lower elastic sealing mechanism from the breathable support plate; and the upper elastic sealing mechanism keeps in contact with the breathable support plate of the upper insect breeding layer that is adjacent to and in contact with the insect breeding layer.

Preferably, the upper elastic sealing mechanism includes a connecting plate and a large elastic tube; the connecting plate includes one end provided on the front baffle or the rear baffle and the other end fixed to the large elastic tube; the lower elastic sealing mechanism includes a connecting plate and a small elastic tube; and the connecting plate includes one end provided on the front baffle or the rear baffle and the other end fixed to the small elastic tube.

Preferably, the sliding power mechanism includes an electric push rod; and the electric push rod includes one end fixed to the frame and the other end fixed to the front baffle or the rear baffle.

Preferably, two sides of the breathable support plate are provided with slotted collection pipes. The present disclosure further provides a breeding and air drying method for a saprophagous insect, implemented by the breeding and air drying system for a saprophagous insect, and including the following steps:

(1) putting larvae of a saprophagous insect and a feed together on the insect breeding layer, and controlling a temperature, a humidity, and oxygen content required for breeding the saprophagous insect;

(2) when air drying is needed at the end of breeding: closing the breeding air inlet of an insect breeding layer that needs air drying and the breeding air inlet of an adjacent insect breeding layer below, closing the air outlet of the adjacent insect breeding layer below, and opening the drying air inlet of the adjacent insect breeding layer below such that the dry hot air passes through the insect breeding layer that needs air drying and flows out from the air outlet of the insect breeding layer that needs air drying, thereby achieving in-situ air drying of a residual feed and the larvae; and (3) allowing, during air drying, the larvae to be heated and flip in the residual feed, playing a role in loosening, flipping, and stirring the material, thereby greatly improving an air drying efficiency.

Preferably, step (2) uses an intermittent air drying mode, including: air-drying for a period of time, pausing for a period of time, and repeating the air-drying and the pausing, where during air drying, mature larvae flip from a lower layer to an upper layer, while during pausing, the mature larvae flip from the upper layer to the lower layer; and repetition of the air-drying and the pausing, the material on the air-dried insect breeding layer is loosened and flipped, thereby improving breathability and the air drying efficiency.

Preferably, the dry hot air is high-pressure dry hot air.

The present disclosure has following beneficial effects:

The breeding and air drying system of the present disclosure can simultaneously carry out breeding and air drying operations, effectively reducing device investment and breeding costs.

Compared with general drying devices, the insect breeding layer of the breeding and air drying system of the present disclosure can provide a larger surface area, facilitating the spreading of the residual feeds and larvae, thereby effectively improving thermal efficiency and reducing costs.

In the present disclosure, during operation, the pressure of the dry hot air is higher than that of the air. According to the principle of resistance, most of the dry hot air flows through a lower air drying layer and is discharged from the air outlet. In addition, during breeding, the breeding time of different layers can be controlled to ensure that the amount of the remaining material in the adjacent layer of the air-dried layer is greater than that in the air-dried layer. In this way, the high-pressure air faces greater resistance when passing through the adjacent layer of the air-dried layer, making it easier to flow towards the air-dried layer. Assuming a material thickness of 10 cm during normal breeding, the material thickness will be reduced by approximately half, that is, to be about 5 cm, after breeding.

During air drying, the air is generally at 30-70° C. The larvae in the adjacent layer of the air-dried layer will get in the material to avoid high-temperature damage. In addition, during air drying, intermittent air drying mode can be used. Specifically, air drying is carried out for a period of time and paused for a period of time, and air drying and pausing are repeated. During pausing, mature larvae move and loosen the material in the air-dried layer, making it breathable and dry.

In the present disclosure, the length of the support fabric is three times the length of the insect breeding layer. During the spreading and breeding processes, the support fabric of a spreading section is located inside a breeding box during breeding and above the breathable support plate during discharging. In this way, the support fabric wound around the spreading roller and the larvae collection roller does not come into contact with the material, effectively solving the problem that the support fabric deviates due to residual material on the support fabric.

In the present disclosure, the breeding box is sealed by the upper elastic sealing mechanism and the lower elastic sealing mechanism. During discharging, the lower elastic sealing mechanism moves up and down and detaches from the support fabric. In this way, the material on the support fabric during discharging is subjected to an even stress and can be completely discharged, effectively solving the problem of residual material in the discharging process in the prior art.

BRIEF DESCRIPTION OF THE DRAWINGS

To describe the technical solutions in the embodiments of the present disclosure or in the prior art more clearly, the following briefly describes the drawings required for describing the embodiments or the prior art. Apparently, the drawings in the following description show merely some embodiments of the present disclosure, and those skilled in the art may still derive other drawings from these drawings without creative efforts.

Reference Signs: 1. baffle; 2. drying air inlet; 3. breathable support plate; 4. bottom sealing layer; 5. breeding air inlet; 6. upper cover; 7. air outlet; 8. frame; 9. insect breeding layer; 10. driven gear; 11. left roller; 12. rotating shaft; 13. left baffle; 14. support fabric; 15. breeding air inlet duct; 16. drying air outlet duct; 17. rear baffle; 18. hot air duct; 19. micro motor; 20. breeding air outlet duct; 21. breeding air outlet valve; 22. roller power mechanism; 23. dry hot air inlet valve; 24. front baffle; 25. breeding air inlet valve; 26. right roller; 27. drying air outlet valve; 28. right baffle; 29. linear guide rail; 30. roller motor; 31. driving gear; 32. guide rail motor; 33. spreading roller; 34. larvae collection roller; 35. inert roller; 36. roller drive motor; 37. electric push rod; 38. sliding groove; 39. slider; 40. pull rope; 41. fabric belt; 42. large elastic tube; 43. connecting plate; 44. small elastic tube; and 45. collection pipe.

DETAILED DESCRIPTION OF THE EMBODIMENTS

The technical solutions of the embodiments of the present disclosure are clearly and completely described below with reference to the drawings in the embodiments of the present disclosure. Apparently, the described embodiments are merely a part rather than all of the embodiments of the present disclosure. All other embodiments obtained by those of ordinary skill in the art based on the embodiments of the present disclosure without creative efforts should fall within the protection scope of the present disclosure.

Embodiment 1

Figure 1:
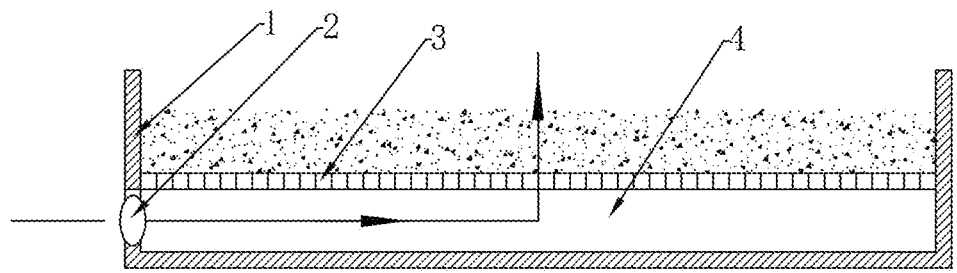
FIG. 1 is a schematic diagram of an air drying structure according to Embodiment 1 of the present disclosure.

The present disclosure provides a breeding and air drying system for a saprophagous insect. As shown in FIG. 1, the breeding and air drying system can achieve breeding and air drying operations, and includes a breeding platform and an air drying system. The breeding platform includes bottom sealing layer 4 and a plurality of insect breeding layers 9. In this embodiment, one insect breeding layer 9 is shown. The insect breeding layer 9 includes a breathable support plate 3 and baffle 1 provided around the breathable support plate 3. The air drying system includes drying air inlet 2 provided below the breathable support plate 3. The drying air inlet 2 is connected to an inlet of hot air duct 18. The hot air duct 18 is configured to provide dry hot air with an air drying effect.

An upper part of the breeding platform is not provided with any upper cover 6, and the breeding platform offers open breeding. This breeding method is extensive and not conducive to regulating the breeding environment. An operation process of this embodiment is as follows.

During the breeding process of insect larvae, the drying air inlet 2 is closed, and open breeding is carried out. After the breeding is completed, the drying air inlet 2 is opened for drying with the dry hot air. The dry hot air enters from a lower part of the breathable support plate 3 to dry the insect larvae and frass on the insect breeding layer 9. During the air drying process, the larvae are heated and flip in the residual feed, playing a role in loosening, flipping, and stirring the materials, greatly improving the air drying efficiency.

Embodiment 2

Figure 2:
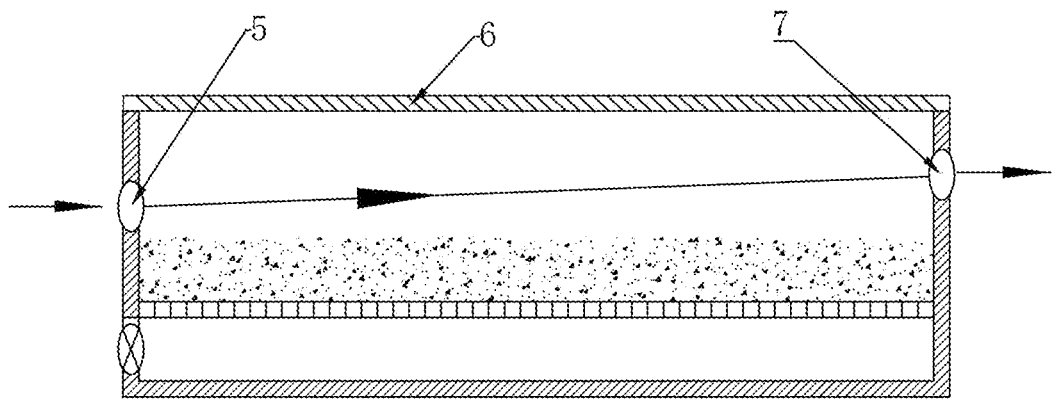
FIG. 2 is a schematic diagram of a breeding drying structure according to Embodiment 2 of the present disclosure.
Figure 3:
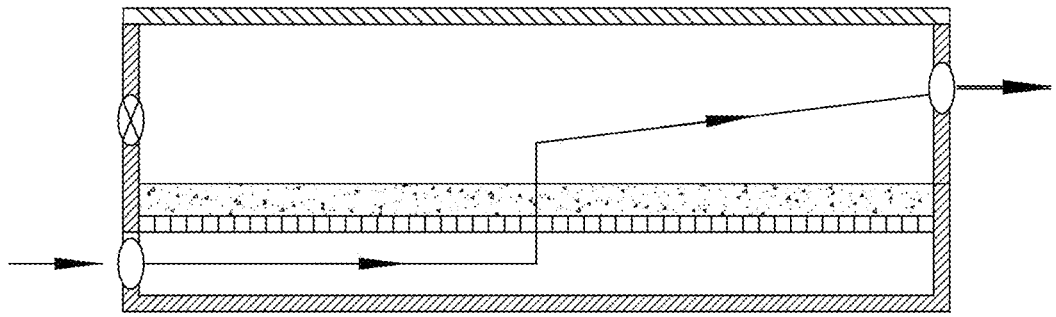
FIG. 3 is a schematic diagram of an air drying structure according to Embodiment 2 of the present disclosure.
Figure 4:
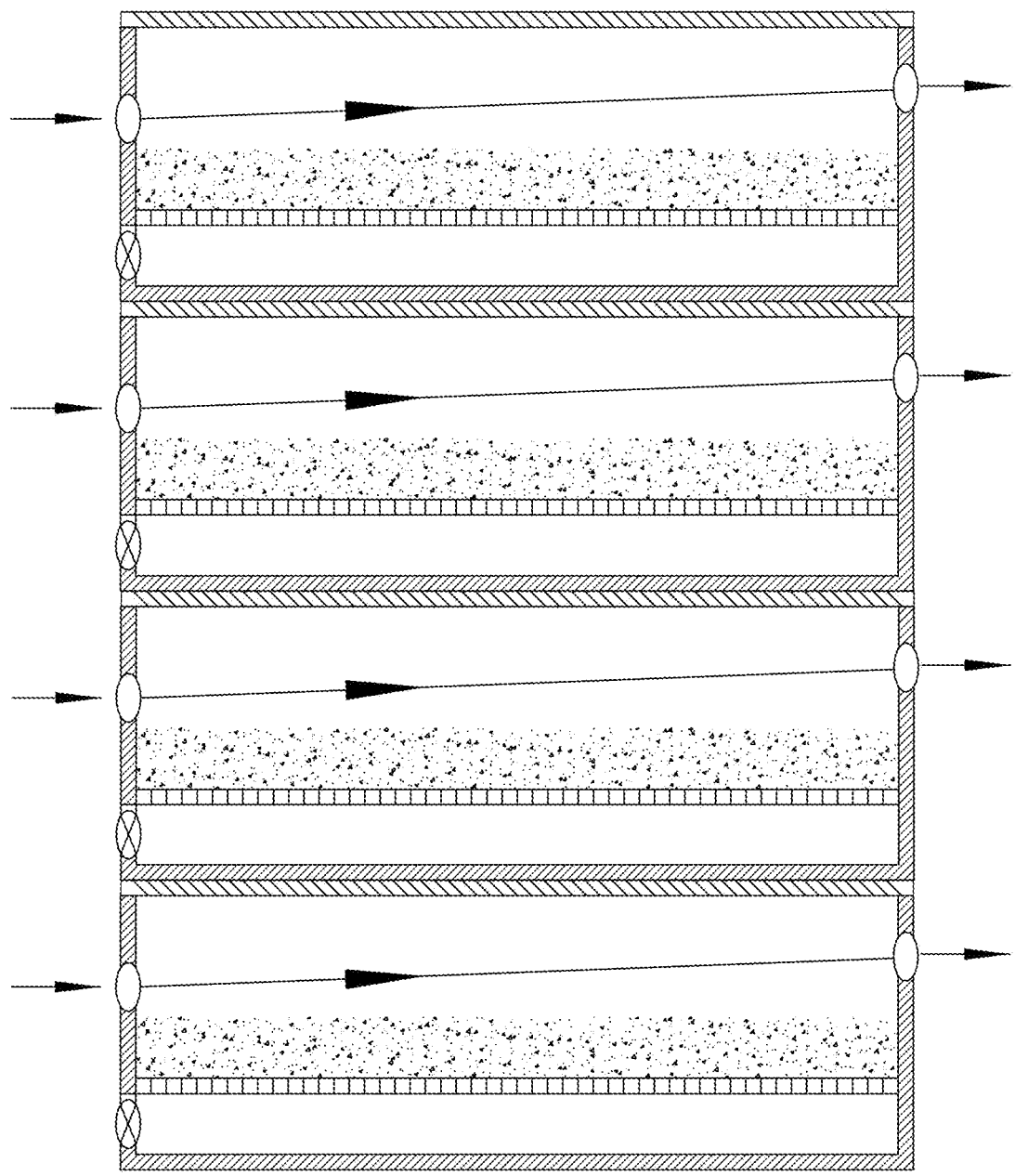
FIG. 4 is a schematic diagram of another breeding structure according to Embodiment 2 of the present disclosure.

As shown in FIGS. 2 to 4, this embodiment is basically the same as Embodiment 1, with the following differences. The upper part of the breeding platform is provided with the upper cover 6, and the upper cover 6 can be opened for charging and discharging operations. In this embodiment, the upper cover 6 is directly pressed onto the baffle 1 to achieve a sealing effect through its own gravity. Of course, the upper cover 6 and the baffle 1 can also be flexibly mounted together in other ways to achieve the sealing effect. The upper cover 6 changes the entire breeding platform into a sealed whole, facilitating precise control of the breeding environment and improving breeding efficiency.

The breeding and air drying system further includes a ventilation system. The ventilation system includes breeding air inlet 5 provided above or below the breathable support plate 3 and air outlet 7 provided above the breathable support plate 3. The breeding air inlet 5 is connected to breeding air inlet duct 15. The breeding air inlet duct is configured to provide a gas for controlling the temperature, humidity, and oxygen content of the breeding space.

An operation process of this embodiment is as follows. As shown in FIG. 2, during normal breeding, the breeding air inlet 5 is opened, and the drying air inlet 2 is closed. The breeding air inlet duct provides the gas for controlling the temperature, humidity, and oxygen content of the breeding space, so as to control the breeding environment. As shown in FIG. 3, when air drying is needed, the breeding air inlet 5 is closed, and the drying air inlet 2 is opened. The dry hot air enters from the lower part of the breathable support plate 3 to dry the insect larvae and frass on the insect breeding layer 9.

As shown in FIG. 4, the structure of this embodiment can be taken as a whole for multi-layer breeding to improve the breeding density.

Embodiment 3

Figure 5:
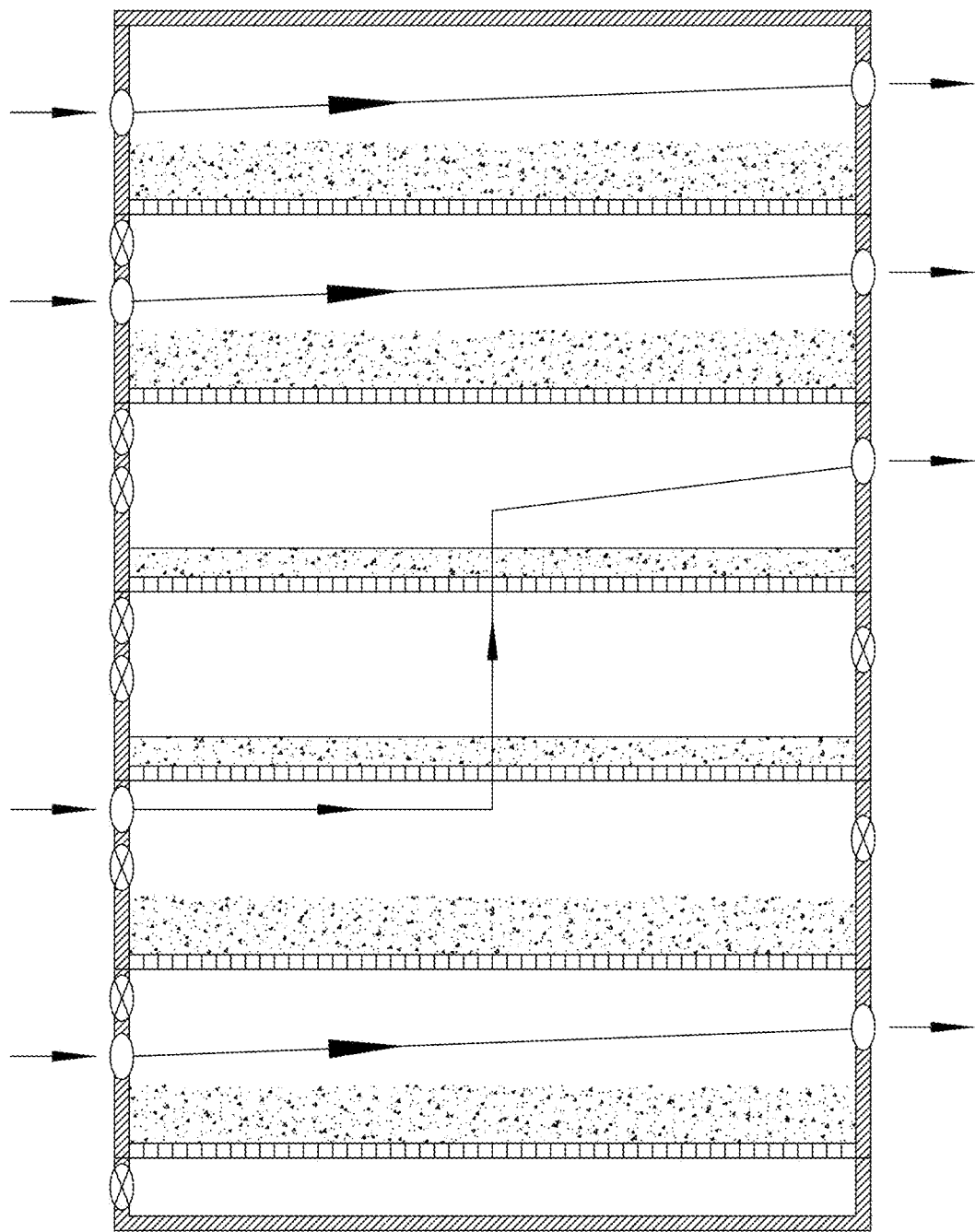
FIG. 5 is a schematic diagram of an air drying structure according to Embodiment 3 of the present disclosure.
Figure 6:
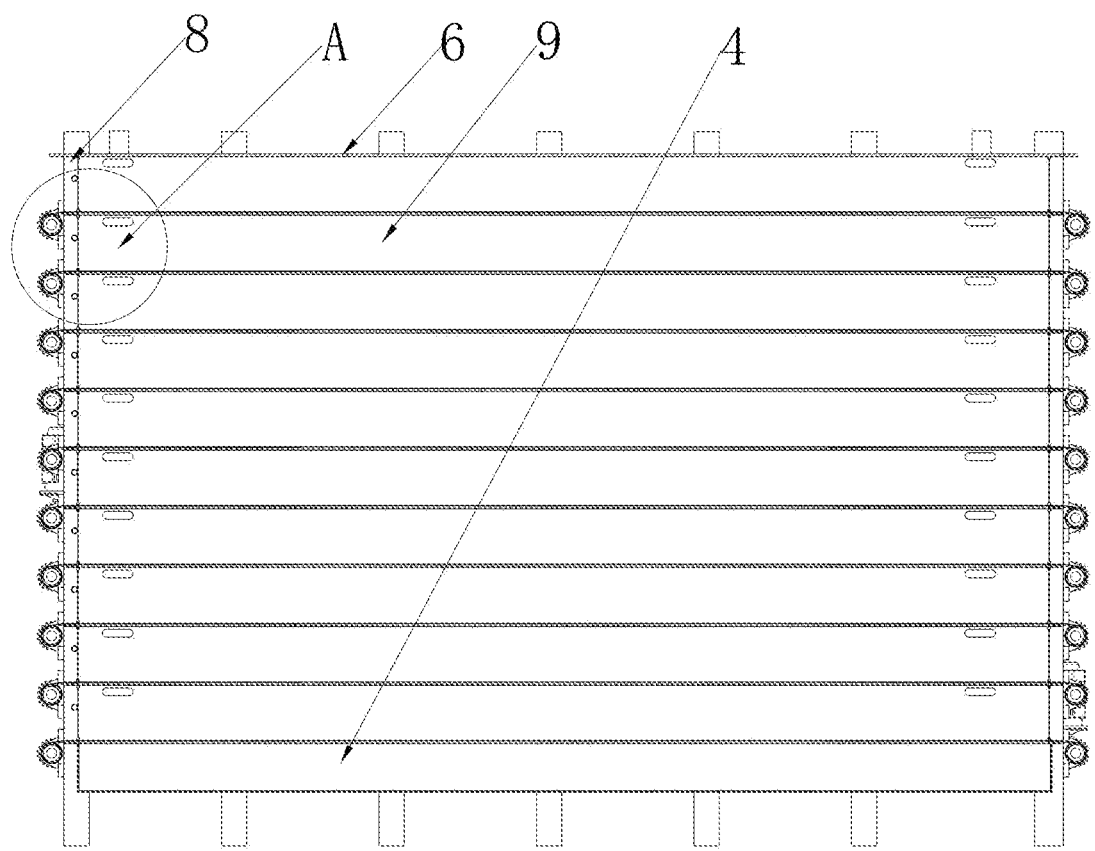
FIG. 6 is a schematic diagram of a plane structure according to Embodiment 4 of the present disclosure.
Figure 7:
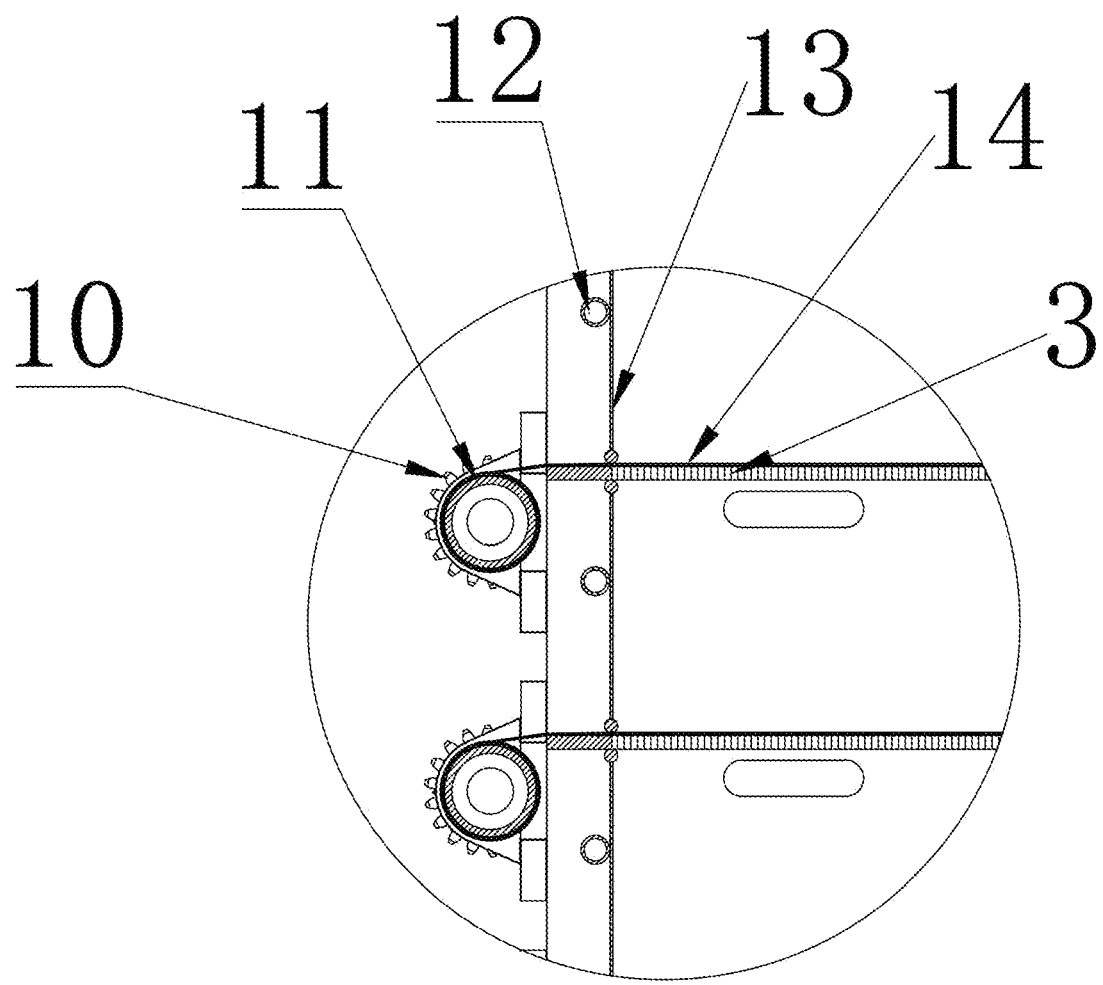
FIG. 7 is an enlarged view of A shown in FIG. 1.
Figure 8:
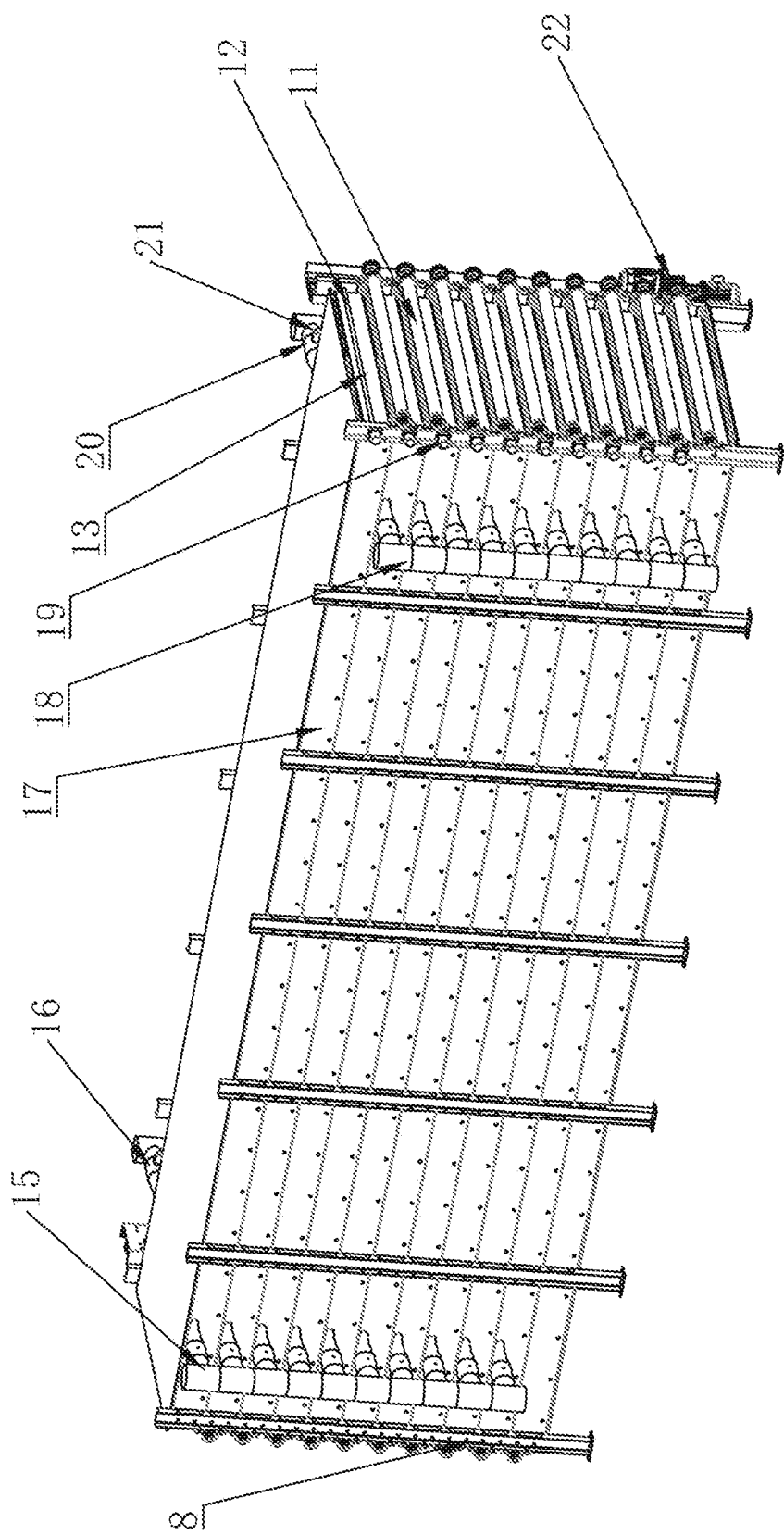
FIG. 8 is a schematic diagram of a stereoscopic structure according to Embodiment 4 of the present disclosure.
Figure 9:
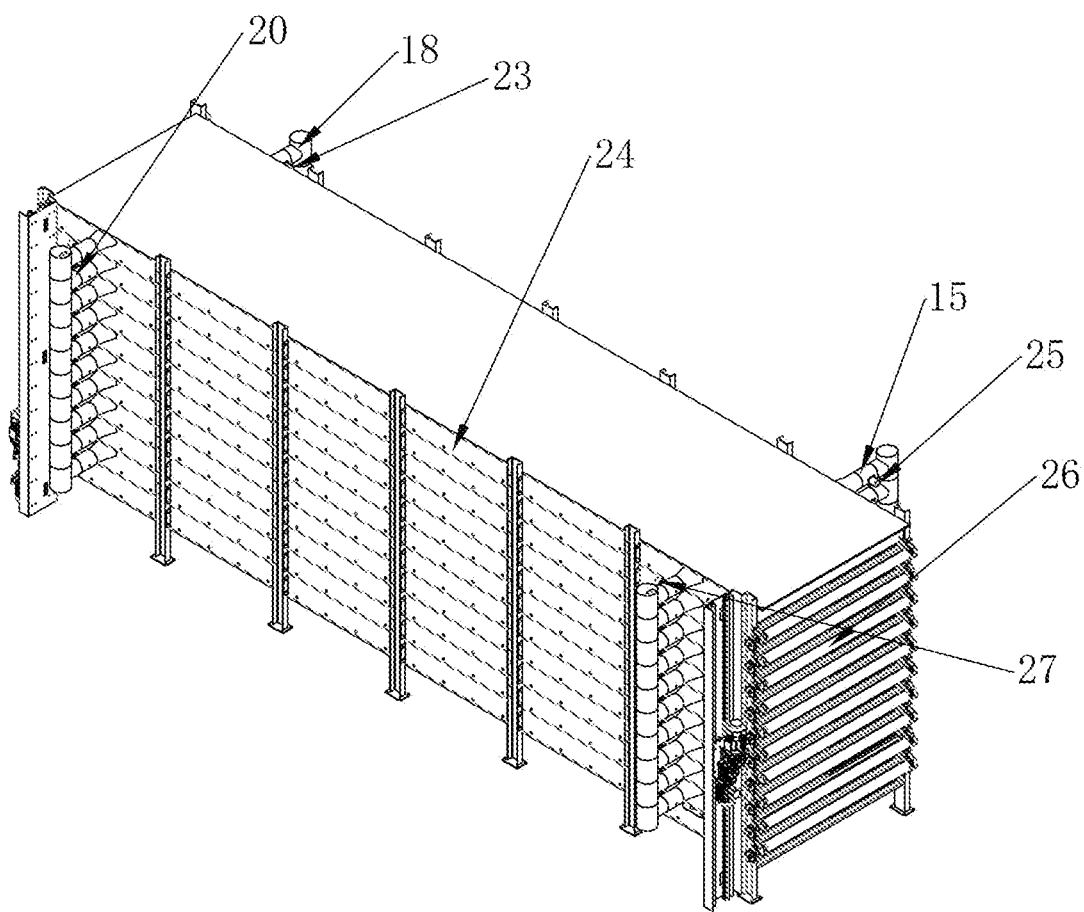
FIG. 9 is a schematic diagram of another stereoscopic structure according to Embodiment 4 of the present disclosure.
Figure 10:
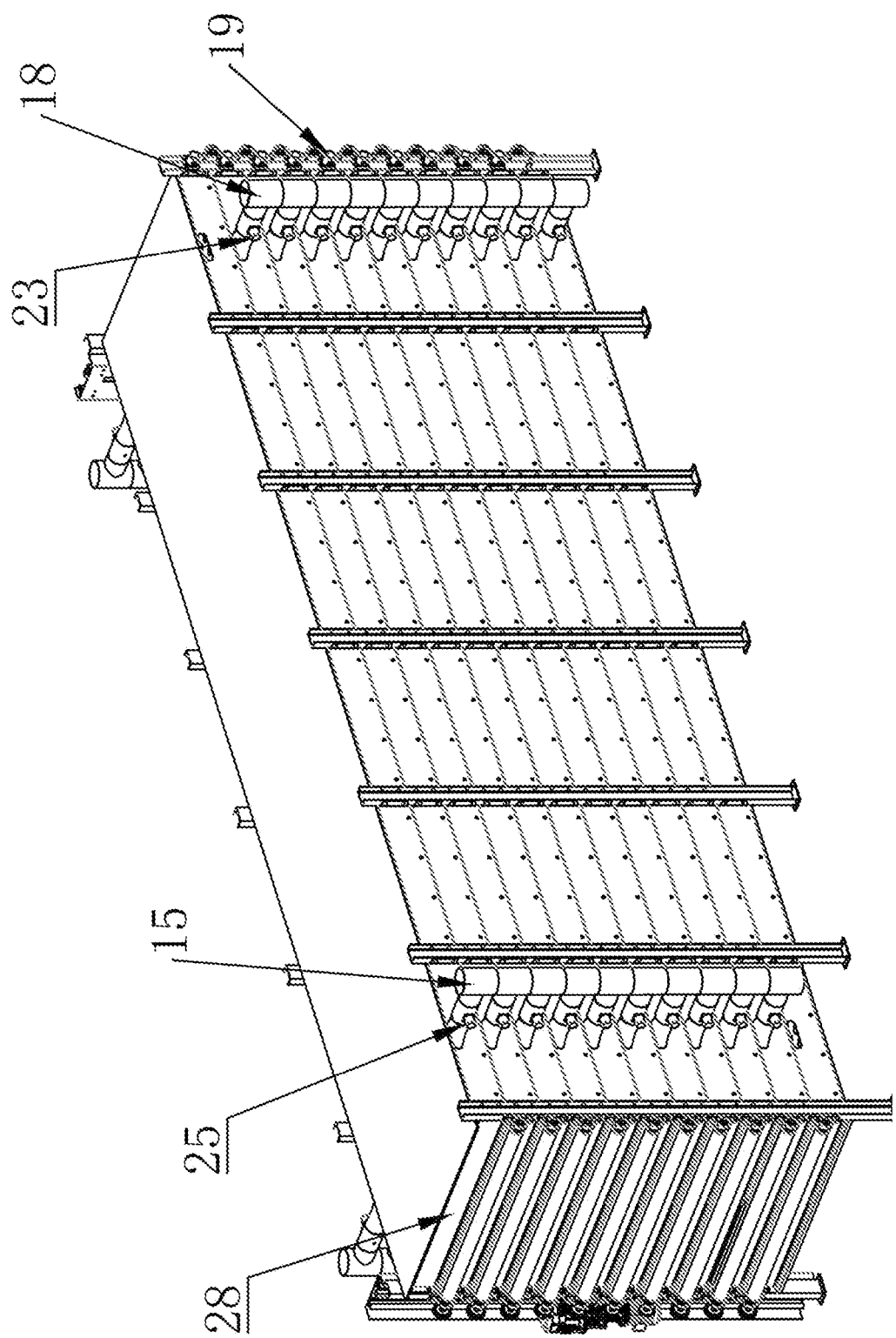
FIG. 10 is a schematic diagram of yet another stereoscopic structure according to Embodiment 4 of the present disclosure.
Figure 11:
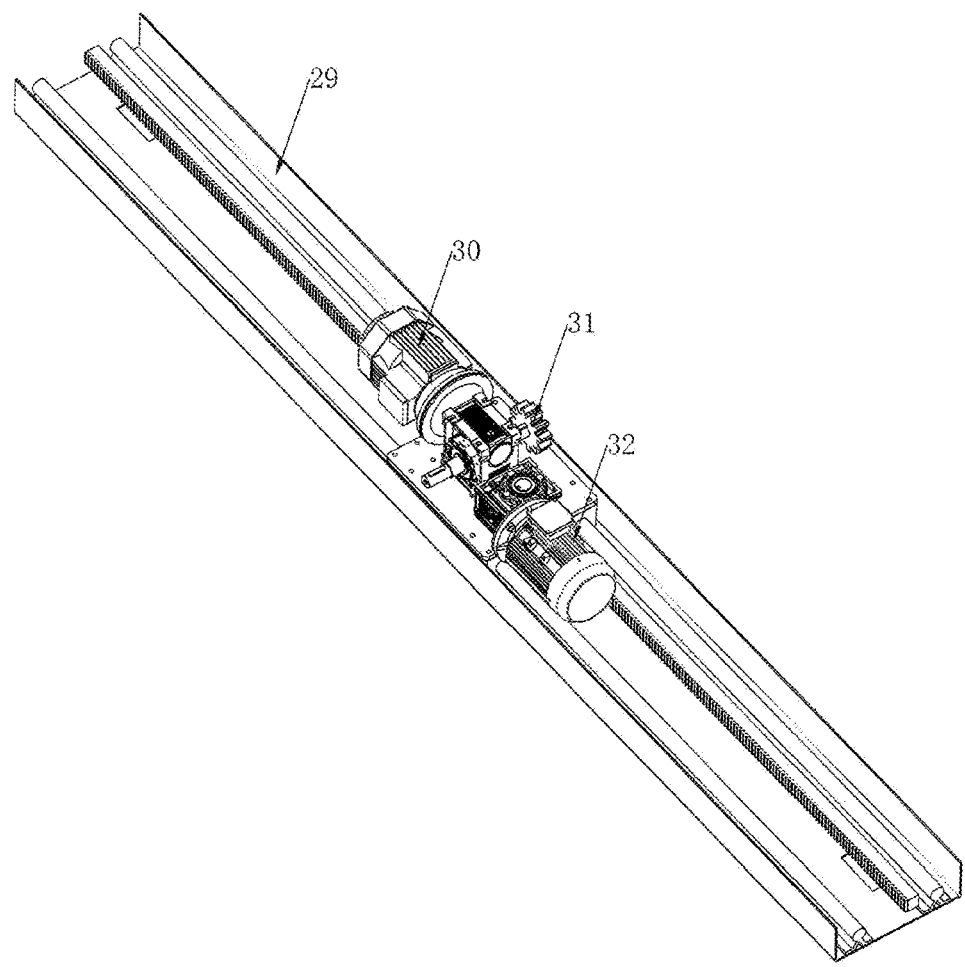
FIG. 11 is a schematic diagram of a stereoscopic structure of a roller power mechanism according to the present disclosure.
Figure 12:
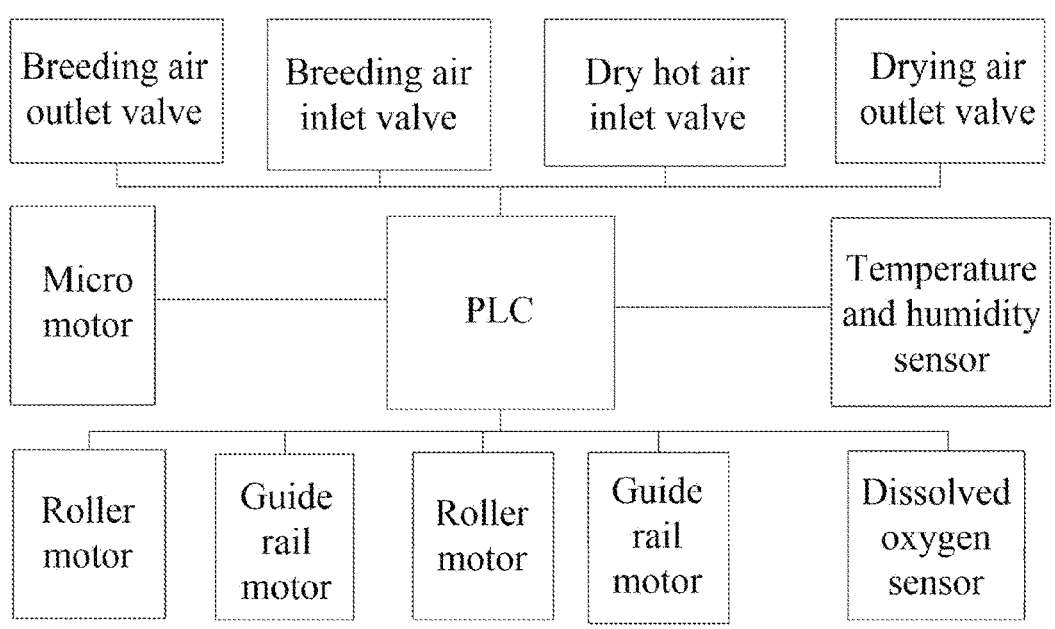
FIG. 12 is a block diagram of a control system according to the present disclosure.

As shown in FIG. 5, this embodiment is basically the same as Embodiment 1, with the following differences. In this embodiment, the upper part of the breeding platform is provided with the upper cover 6, and the upper cover 6 can be opened for charging and discharging operations. In this embodiment, there are 6 insect breeding layers 9. The breeding and air drying processes of this embodiment are basically the same as those described in the above embodiment, with the following differences. In this embodiment, there are two layers for simultaneous air drying, specifically, third and fourth layers for simultaneous air drying. During the air drying operation, first, fifth, and sixth layers carry out normal ventilation for the breeding operation. The breeding air inlets 5 on the second to fourth layers and the air outlets 7 on the second and third layers are closed. The drying air inlet 2 on the second layer is opened, so the dry hot air enters from the drying air inlet on the second layer. The larvae on the second layer get in the material to avoid high-temperature damage. The dry hot air passes through the third and fourth layers and is discharged from the air outlet 7 of the fourth layer to dry the larvae and frass.

Embodiment 4

Embodiments 2 and 3 both provide multiple layers for breeding, but during the charging and discharging process, it is necessary to move the insect breeding layers 9, which is a complex operation.

This embodiment provides a breeding and air drying system for a saprophagous insect. As shown in FIGS. 6 to 12, the breeding and air drying system can achieve breeding and air drying operations, and includes a breeding platform and an air drying system. The breeding platform includes bottom sealing layer 4 and a plurality of insect breeding layers 9. The insect breeding layer 9 includes a breathable support plate 3 and baffle 1 provided around the breathable support plate 3.

The insect breeding layer 9 further includes support fabric 14, left roller 11, right roller 26, and roller power mechanisms 22. The baffle 1 includes front baffle 24, rear baffle 17, left baffle 13, and right baffle 28. The support fabric 14 is in contact with the breathable support plate 3. Two ends of the support fabric 14 are respectively wound around the left roller 11 and the right roller 26. The left roller 11 and the right roller 26 are fixed to frame 8. The left roller 11 and the right roller 26 are respectively connected to the roller power mechanisms 22. The roller power mechanisms 22 are respectively configured to drive the left roller 11 and the right roller 26 to rotate. The left baffle 13 and/or the right baffle 28 are movable structures that can be opened and closed. When the left baffle 13 and right baffle 28 are closed, the support fabric 14 and the breathable support plate 3 are tightly sealed. The left baffle 13 and/or the right baffle 28 each are fixed to the frame 8 through rotating shaft 12. The rotating shaft 12 is connected to rotating shaft 12 power mechanism. In this embodiment, the left baffle 13 is a movable structure, and the right baffle 28 is a fixed structure. The rotating shaft 12 power mechanism is configured to drive the opening and closing of the baffle. The rotating shaft power mechanism can be a power device in the prior art, such as a hydraulic cylinder, and in this embodiment, it is micro motor 19.

The roller power mechanism 22 is configured to drive the roller to rotate and achieve the wind-up and wind-off of the support fabric 14. Power motors with automatic clutches, or servo motors, can be mounted at two ends of each layer. However, such a structure makes a bulky device and high cost. In this embodiment, the roller power mechanism 22 includes linear guide rail 29, guide rail motor 32, roller motor 30, driven gear 10 provided at an end of the roller, and driving gear 31 provided at an end of the roller motor 30. The roller motor 30 is fixed to a slider of the linear guide rail 29. The guide rail motor 32 drives the linear guide rail 29 to move. During operation, the guide rail motor 32 drives the slider to move in a straight line, which in turn drives the roller motor 30 to move to a roller desired to move. The driven gear 10 at an end of the roller meshes with the driving gear 31 at an end of the roller motor 30. The guide rail motor 32 stops moving, and the roller motor 30 is started to drive the roller to rotate for the wind-up and wind-off of the support fabric 14.

The air drying system includes drying air inlet 2 provided below the breathable support plate 3. The drying air inlet 2 is connected to an inlet of hot air duct 18. The hot air duct 18 is configured to provide dry hot air with an air drying effect.

A top of the breeding platform is provided with the upper cover 6.

The breeding and air drying system further includes a ventilation system. The ventilation system includes breeding air inlet 5 provided above or below the breathable support plate 3 and air outlet 7 provided above the breathable support plate 3. The breeding air inlet 5 is connected to breeding air inlet duct 15. The breeding air inlet duct is configured to provide a gas for controlling the temperature, humidity, and oxygen content of the breeding space. In this embodiment, the air outlet 7 is provided on an upper part of the breathable support plate 3.

The breeding air inlet 5, the air outlet 7, and the drying air inlet 2 are provided according to actual needs. For example, they are provided at each layer, at every other layer, or at two sides. In order to achieve precise control of breeding and air drying, the following solution is adopted in this embodiment. Except for the top insect breeding layer, each of the other insect breeding layers 9 is provided with the breeding air inlet 5, the air outlet 7, and the drying air inlet 2. The breeding air inlet duct 15 is provided with breeding air inlet valve 25. An air outlet duct is provided with an air outlet valve. The hot air duct 18 is provided with dry hot air inlet valve 23. In this embodiment, the breeding air inlet 5 and the drying air inlet 2 are provided at two sides in one direction of the system, and two air outlets 7, namely a breeding air outlet and a drying air outlet, are provided at two sides in the other direction of the system. The breeding air outlet is provided on the breeding air outlet duct 20, and breeding air outlet valve 21 is provided on the breeding air outlet duct 20. The drying air outlet is provided on drying air outlet duct 16, and drying air outlet valve 27 is provided on the drying air outlet duct 16. In this implementation, during breeding, the breeding air outlet valve 21 is opened, and the drying air outlet valve 27 is closed. During air drying, the breeding air inlet valve is opened, and the breeding air outlet valve 21 is closed.

Alternatively, the breeding air inlet 5 and the drying air inlet 2 are provided at the same side in one direction of the system, and one air outlet is provided at one side in the other direction of the system.

The breeding and air drying system further includes a temperature and humidity sensor and a control system. The breeding air inlet valve 25 and the hot air inlet valve are electric valves. The breeding air inlet valve 25 and the hot air inlet valve are connected to the control system, respectively. The temperature and humidity sensor is provided at the air outlet. In order to better control the breeding environment, the temperature and humidity sensor and another sensor such as a dissolved oxygen sensor (not shown in the figure) can be provided on the insect breeding layer 9, which is a conventional configuration. The sensor can be mounted in any appropriate position as needed to control the breeding environment. In this embodiment, the temperature and humidity sensor is mounted at the air outlet to measure the temperature and humidity of the air outlet during air drying. If the temperature and humidity of the air outlet are too low and cannot achieve the purpose of fully utilizing heat, the valve at the air outlet is closed, allowing the hot air to continue to flow upwards and be discharged from the above air outlet, thereby achieving the purpose of fully utilizing heat.

The control system is a programmable microcontroller or programmable logic controller (PLC). In this embodiment, the control system is a programmable microcontroller.

The air drying process of this embodiment is similar to that in Embodiment 3 and will not be repeated herein.

The charging and discharging processes of this embodiment are as follows.

The charging process is as follows. The control system controls the rotating shaft 12 power mechanism to open the left baffle 13 of the insect breeding layer, and a charging port of a charging mechanism extends into the insect breeding layer 9. The guide rail motor 32 drives the slider to move in a straight line, which in turn drives the roller motor 30 to move to the right roller 26 desired to move. The driven gear 10 at one end of the right roller 26 meshes with the driving gear 31 at an end of the roller motor 30. The guide rail motor 32 stops moving, and the roller motor 30 is started to drive the roller to rotate for the wind-up and wind-off of the support fabric 14. The charging mechanism moves to transport the material to the support fabric 14. The support fabric 14 is driven by the roller to move to the right and transports the material from left to right. In this way, the support fabric moves while spreading the material, thereby completing the material spreading operation.

The discharging process is as follows. The control system controls the rotating shaft 12 power mechanism to open the left baffle 13 of the insect breeding layer, and a charging port of a discharging mechanism extends into the insect breeding layer 9. The guide rail motor 32 drives the slider to move in a straight line, which in turn drives the roller motor 30 to move to the left roller 11 desired to move. The driven gear 10 at one end of the left roller 11 meshes with the driving gear 31 at an end of the roller motor 30. The guide rail motor 32 stops moving, and the roller motor 30 is started to drive the roller to rotate for the wind-up and wind-off of the support fabric 14. The material is collected from the support fabric 14 and enters the discharging mechanism through the discharging port, thereby completing the discharge.

Alternatively, the left baffle and the right baffle are movable structures, and the charging mechanism and the discharging mechanism are respectively provided at two ends of the breeding platform to achieve simultaneous charging and discharging operations, effectively improving device utilization.

Embodiment 5

This embodiment provides a breeding and air drying method for a saprophagous insect, implemented by the breeding and air drying system for a saprophagous insect in Embodiment 5, and including the following steps.
(1) The larvae of the saprophagous insect and feed are put together on the insect breeding layer 9, and a temperature, a humidity, and oxygen content required for breeding the saprophagous insect are controlled.
(2) When air drying is needed at the end of breeding, the breeding air inlet 5 of the insect breeding layer 9 that needs air drying and the breeding air inlet of an adjacent insect breeding layer 9 below are closed, and the breeding air outlet of the adjacent insect breeding layer below is closed, and the drying air inlet of the adjacent insect breeding layer below is opened such that the dry hot air passes through the insect breeding layer 9 that needs air drying and flows out from the air outlet of the insect breeding layer 9 that needs air drying, thereby achieving in-situ air drying of a residual feed and the larvae.
(3) During air drying, the larvae are heated and flip in the residual feed, playing a role in loosening, flipping, and stirring the material, greatly improving the air drying efficiency.

In step (2), an intermittent air drying mode is used. Specifically, air-drying is carried out for a period of time and paused for a period of time, and air-drying and pausing are repeated. During air drying, mature larvae flip from a lower layer to an upper layer, while during pausing, mature larvae flip from the upper layer to the lower layer. The air-drying and the pausing are repeated to loosen and flip the material on the air-dried insect breeding layer, thereby improving breathability and air drying efficiency.

The dry hot air is high-pressure dry hot air. In the present disclosure, the pressure of the high-pressure dry hot air needs to be higher than an external pressure of the breeding and air drying system. Generally, a higher pressure is more conducive to the flow of the dry hot air. However, an excessive pressure can lead to an increase in the air drying cost, so the pressure is generally set according to an actual need.

The air drying effects were tested.

The test materials were collected when the larvae of *Hermetia illucens* were bred for 10 days, which had a moisture content of 61.6% and were composed of the larvae and frass with a ratio of 1:2. Each drying method was tested 5 times, using 100 kg of materials.

Drying method 1. The larvae and the frass were not separated, but were directly dried by a roller dryer to a moisture content of 25%. Then the larvae and the frass were separated by screening, and an energy consumption and a larvae yield were calculated.

Drying method 2. The single-layer structure of Embodiment 2 was adopted. The insect breeding layer 9 had an area of 5 m2, and 100 kg of materials were evenly spread on the insect breeding layer 9. Continuous air drying was carried out at 47° C. and 1,210 pa until the larvae and frass were dried to a 25% moisture content. An energy consumption and a larvae yield were calculated.

Drying method 3. The single-layer structure of Embodiment 2 was adopted. The insect breeding layer 9 had an area of 5 m2, and 100 kg of materials were evenly spread on the insect breeding layer 9. Intermittent air drying was carried out. Specifically, air drying was carried out at 47° ° C. and 1,210 pa for 3 min, and was paused for 2 min. The air drying and pausing were repeated until the frass and larvae were dried to a 25% moisture content. An energy consumption and a larvae yield were calculated. The test data are shown in the table below.

|  | Energy consumption (Kw · h) | Larvae yield (kg) |
|---|---|---|
| Drying method 1 | 28.25 + 0.29 | 25.10 + 0.25 |
| Drying method 2 | 11.80 + 0.14** | 28.93 + 0.15** |
| Drying method 3 | 10.56 + 0.22**# | 28.25 + 0.28** |

Note:
*indicates a significant difference, P < 0.05;
**indicates a highly significant difference, P < 0.01 vs air drying method 1;
indicates significant difference, P < 0.05; and
indicates a highly significant difference, P < 0.01 vs air drying method 2.

According to the above table, compared to traditional methods, the air drying method of the present disclosure saves more than 139% energy and has good effects. Compared to the continuous air drying method, the intermittent air drying method of the present disclosure saves 12% energy and has significant advantages.

In terms of the larvae yield, the method of the present disclosure significantly increases the larvae yield by more than 12%. Therefore, the device and method of the present disclosure have obvious advantages in the breeding and air drying of *Hermetia illucens* larvae.

Embodiment 6

Figure 13:
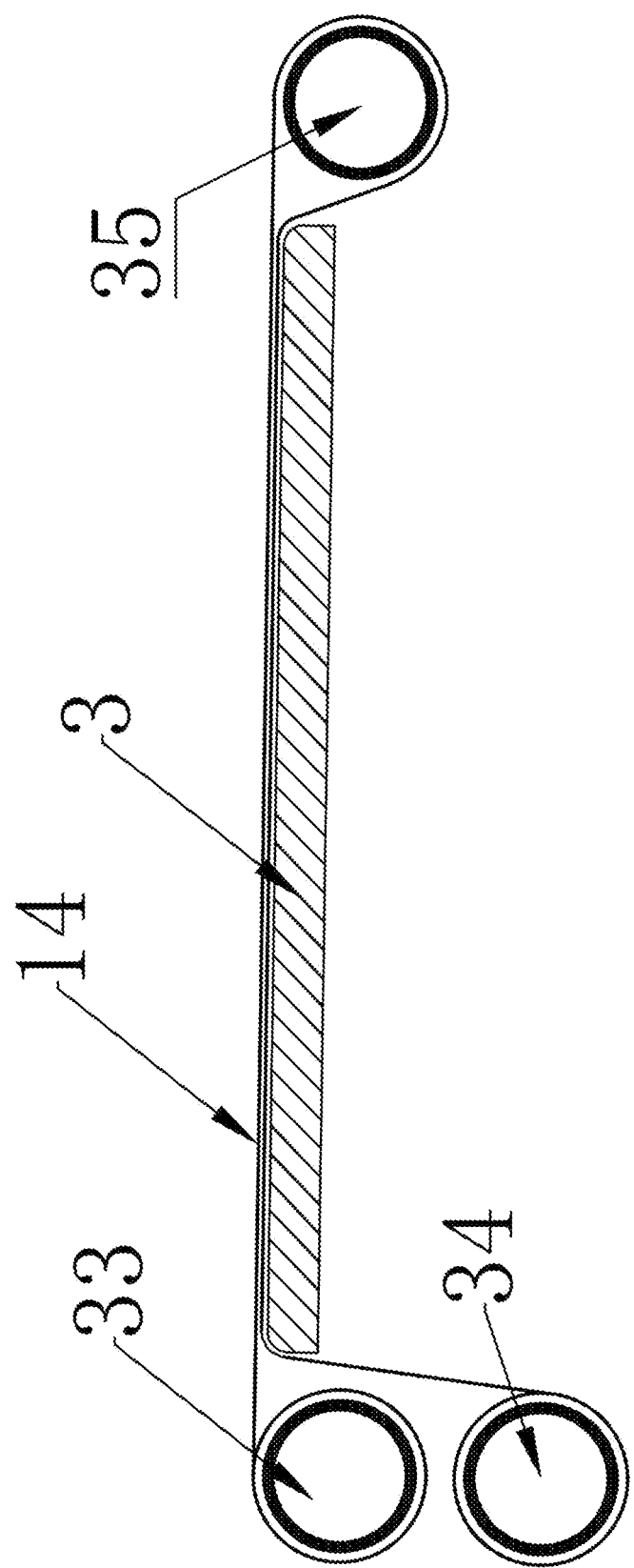
FIG. 13 is a structural schematic diagram according to Embodiment 6 of the present disclosure.
Figure 14:
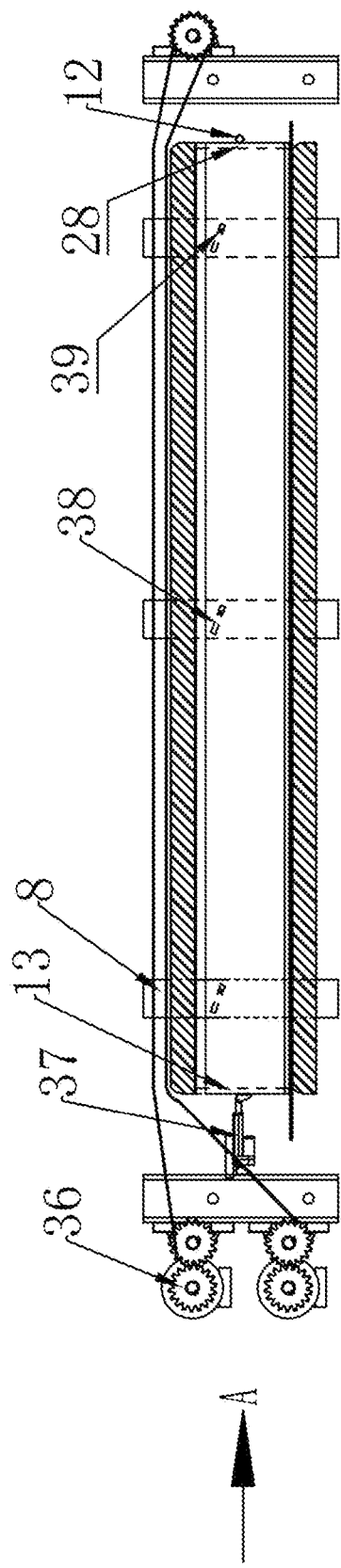
FIG. 14 is a structural schematic diagram according to Embodiment 7 of the present disclosure.

As shown in FIGS. 13 to 14, this embodiment is basically the same as Embodiment 4, except for the following differences.

A breeding and spreading device for a saprophagous insect includes multiple breeding layers and a frame. The insect breeding layer includes one end provided with inert roller 35 and the other end provided with spreading roller 33 and larvae collection roller 34. The spreading roller 33 is provided above the larvae collection roller 34. The spreading roller 33 and the larvae collection roller 34 are provided with a driving mechanism. The support fabric includes one end fixed to the spreading roller 33 and the other end bypassing the inert roller 35, passing from an upper part of the breathable support plate, and fixed to the larvae collection roller 34. A length of the support fabric is three times a length of the insect breeding layer. During breeding, the spreading roller 33 is wound with one part of the support fabric with the same length as the insect breeding layer, and the remaining part of the support fabric is fixed between the spreading roller 33, the inert roller 35, and the larvae collection roller 34.

In this embodiment, one breeding layer is shown, and there is no sealing device above or below the insect breeding layer. In practical application, upper and lower sealing layers can be provided, and multiple breeding layers as shown in this embodiment can be provided.

In this embodiment, the driving mechanism is a conventional device mainly configured to drive the movement of the spreading roller 33 and the larvae collection roller 34. In this embodiment, roller drive motors 36 and meshed gears are provided. One gear is fixed to the spreading roller 33 and the larvae collection roller 34, and the other gear is fixed to the roller drive motor 36. The spreading roller 33 and the larvae collection roller 34 are respectively driven by two roller drive motors 36. Of course, other forms of power mechanisms can also be used as needed. In this embodiment, the driving mechanism can also adopt the structure of Embodiment 4, which will not be repeated herein.

An operation process of this embodiment is as follows.

The spreading process is as follows. The left baffle and the right baffle are opened, and the spreading roller 33 rotates, driving the support fabric to move. The material moves continuously with the support fabric, thus being transported from one end of the insect breeding layer to the other end. The support fabric wound around the spreading roller 33 is not contaminated by the material.

The collection process is as follows. At the end of breeding, the collection roller moves and drives the support fabric to move, allowing the material to be transported from one end of the insect breeding layer to the other end thereof. The material detaches from the support fabric under the action of gravity, thereby completing the material collection operation. During this process, the support fabric wound around the collection roller is located under the support fabric contaminated with the material, and is thus not contaminated by the material.

During the spreading and collection process, the support fabric wound around the spreading roller 33 and the collection roller are not contaminated with the material and are clean. Therefore, during the wind-up and wind-off process, the support fabric is uniform without deviation, ensuring even and labor-saving spreading and collection and effectively extending the service life of the device.

Figure 15:
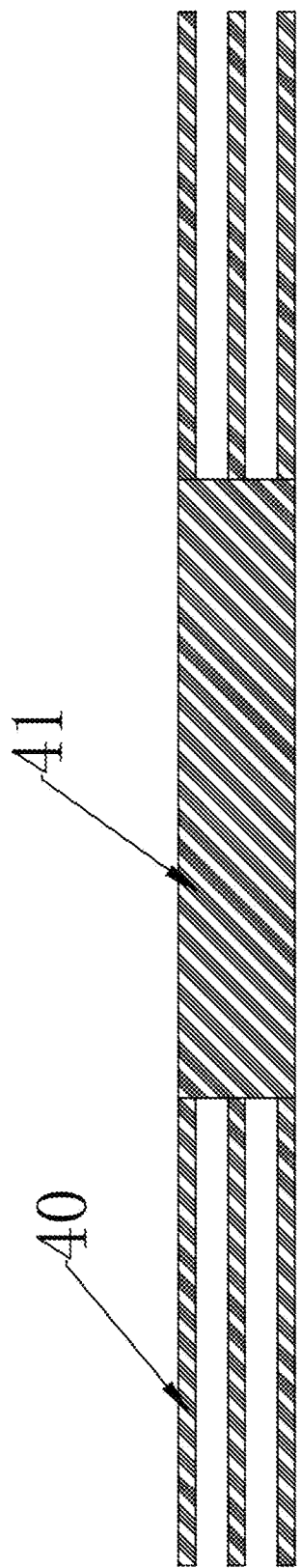
FIG. 15 is a structural schematic diagram of a support fabric according to the present disclosure.
Figure 16:
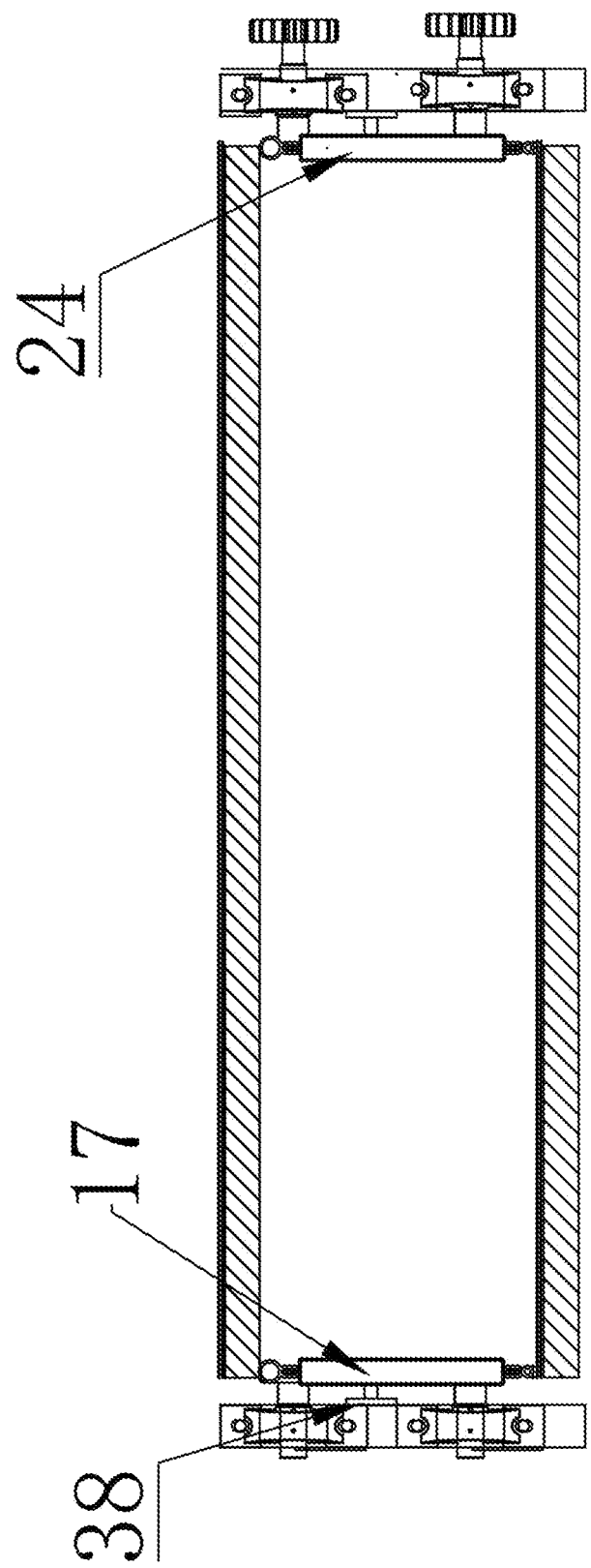
FIG. 16 is a structural schematic diagram along A-direction shown in FIG. 14.
Figure 17:
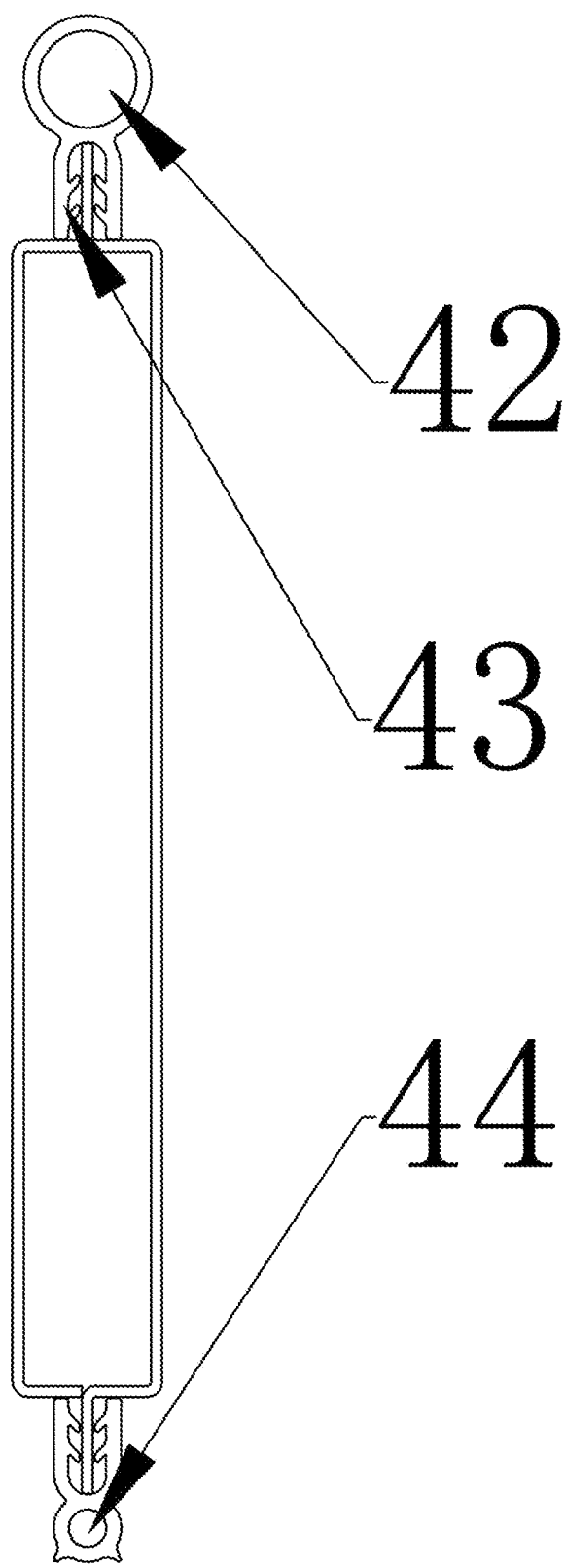
FIG. 17 is a structural schematic diagram of an upper elastic sealing mechanism and a lower elastic sealing mechanism according to the present disclosure.

The support fabric can be a one-piece breathable fabric, plastic mesh, or metal mesh. However, there is a problem that the one-piece support fabric requires a considerable amount of power. Therefore, in the present disclosure, the support fabric can adopt the following structure. As shown in FIG. 15, the support fabric includes a plurality of pull ropes 40 provided at two ends of the support fabric and having the same length as the insect breeding layer and fabric belt 41 provided at a middle. A width of the fabric belt 41 is the same as a width of the insect breeding layer. The structure can effectively reduce the friction force between the support fabric and the spreading roller 33 as well as the collection roller, and effectively reduce energy consumption. Alternatively, the support fabric can include one end provided with the pull ropes and the other end provided with the fabric belt.

Embodiment 7

As shown in FIGS. 14 to 17, a breeding and spreading device for a saprophagous insect includes multiple breeding layers and a frame. The insect breeding layer includes a breathable support plate and a baffle provided around the breathable support plate. The baffle includes a front baffle, a rear baffle, a left baffle, and a right baffle. The left baffle and/or the right baffle are respectively fixed to the frame through a rotating shaft, and the rotating shaft is connected to a rotating shaft power mechanism. In this implementation, the right baffle is fixed to the frame through the rotating shaft, which is connected to the rotating shaft power mechanism (generally electric push rod 37, which is not shown in the figure). The left baffle is fixed to the frame. A lower part of the left baffle is at a certain distance from the support fabric, and a left side is sealed by the gravity of the material.

During spreading and collection processes, the right baffle is opened under the action of the rotating shaft power mechanism, so as to carry out the spreading and collection operations.

Each of the front baffle and the rear baffle is provided in sliding groove 38 of the frame through slider 39. Each of the front baffle and the rear baffle includes an upper end provided with an upper elastic sealing mechanism and a lower end provided with a lower elastic sealing mechanism. An end of each of the front baffle and the rear baffle is connected to a sliding power mechanism. The upper elastic sealing mechanism is in contact with the breathable support plate of an upper insect breeding layer that is adjacent to and in contact with the insect breeding layer. The lower elastic sealing mechanism is in contact with the breathable support plate. The sliding power mechanism drives the front baffle and the rear baffle to move obliquely upwards to separate the lower elastic sealing mechanism from the breathable support plate. The upper elastic sealing mechanism keeps in contact with the breathable support plate of the upper insect breeding layer that is adjacent to and in contact with the insect breeding layer.

The upper elastic sealing mechanism includes connecting plate 43 and large elastic tube 42. The connecting plate 43 includes one end provided on the front baffle or the rear baffle and the other end fixed to the large elastic tube 42. The lower elastic sealing mechanism includes connecting plate 43 and small elastic tube 44. The connecting plate 43 includes one end provided on the front baffle or the rear baffle and the other end fixed to the small elastic tube 44.

The sliding power mechanism includes electric push rod 37. The electric push rod 37 includes one end fixed to the frame and the other end fixed to the front baffle or the rear baffle through a connecting mechanism.

The left baffle and the right baffle are generally long and require a small distance of movement, usually less than 1 cm. If a vertical tension is used, there is a problem of stress imbalance. Therefore, in the present disclosure, the slide way is generally tilted 3-10°. In this way, at one end of the left baffle and the right baffle, an obliquely upwards pull is applied to move the left baffle and the right baffle up and down. The design ensures stress balance and smooth operation of the left baffle and the right baffle.

The insect breeding layer includes one end provided with inert roller 35 and the other end provided with spreading roller 33 and larvae collection roller 34. The spreading roller 33 is provided above the larvae collection roller 34. The spreading roller 33 and the larvae collection roller 34 are provided with a driving mechanism. The support fabric includes one end fixed to the spreading roller 33 and the other end bypassing the inert roller 35 and fixed to the larvae collection roller 34. A length of the support fabric is three times a length of the insect breeding layer. During breeding, the spreading roller 33 is wound with one part of the support fabric with the same length as the insect breeding layer, and the remaining part of the support fabric is fixed between the spreading roller 33, the inert roller 35, and the larvae collection roller 34.

An operation process of this embodiment is as follows.

In this embodiment, the left baffle and the right baffle compress edges of the support fabric onto the breathable support plate. When it is necessary to replenish or discharge the material, the electric push rod 37 drives the left baffle and the right baffle obliquely upwards. The small elastic tube 44 leaves the support fabric, and the large elastic tube 42 is compressed. In this way, during the distribution and collection processes, the edges of the support fabric are evenly stressed, and all materials can be transported, ensuring complete material collection.

Figure 18:
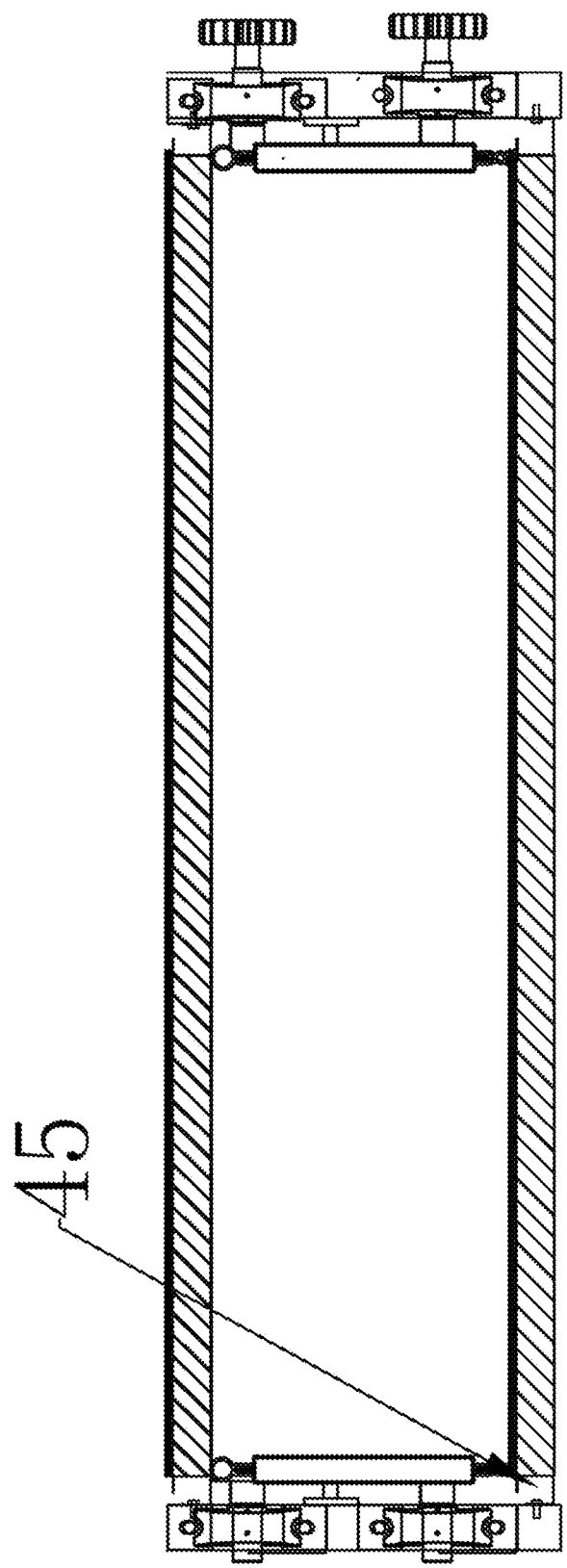
FIG. 18 is another structural schematic diagram along A-direction shown in FIG. 14.

During the collection process, the larvae can escape through a gap between the support fabric and the small elastic tube 44. To this end, collection devices can be provided at two sides of the breathable support plate to collect the escaping larvae. Specifically, the structure of the collection device is designed as needed, as shown in FIG. 18. In the present disclosure, the two sides of the breathable support plate are provided with slotted collection pipes 45. The structure allow the escaping larvae to automatically fall into the collection pipes 45 for unified collection, thereby effectively avoiding the problem of larvae escaping.

Although the embodiments of the present disclosure are described above, modifications and replacements made by those skilled in the art without departing from the principle and spirit of the present disclosure should fall within the protection scope of the present disclosure.

What is claimed is:

1. A breeding and air drying system for a saprophagous insect, configured to carry out breeding and air drying operations, and comprising a breeding platform and an air drying system, wherein the breeding platform comprises a bottom sealing layer and a plurality of insect breeding layers; the plurality of insect breeding layers comprise a breathable support plate and a baffle provided around the breathable support plate; the air drying system comprises a drying air inlet provided below the breathable support plate; the drying air inlet is connected to an inlet of a hot air duct; and the hot air duct is configured to provide dry hot air with an air drying effect;

wherein a top of the breeding platform is provided with an upper cover;

the breeding and air drying system further comprises a ventilation system; the ventilation system comprises a breeding air inlet provided above or below the breathable support plate and an air outlet provided above the breathable support plate; the breeding air inlet is connected to a breeding air inlet duct; and the breeding air inlet duct is configured to provide a gas for controlling a temperature, a humidity, and an oxygen content of a breeding space;

except for a top insect breeding layer, each of the plurality of insect breeding layers is provided with the breeding air inlet, the air outlet, and the drying air inlet; the breeding air inlet duct is provided with a breeding air inlet valve; an air outlet duct is provided with an air outlet valve; and the hot air duct is provided with a dry hot air inlet valve.

2. The breeding and air drying system for the saprophagous insect according to claim 1, wherein the breeding and air drying system further comprises a control system; and the breeding air inlet valve and the hot air inlet valve are electric valves, and the breeding air inlet valve and the hot air inlet valve are connected to the control system, respectively.

3. The breeding and air drying system for the saprophagous insect according to claim 2, wherein a temperature and humidity sensor is provided at the air outlet.

4. The breeding and air drying system for the saprophagous insect according to claim 2, wherein the plurality of insect breeding layers further comprise a front, rear, left, and right portion, a support fabric or support mesh, a left roller, a right roller, and roller power mechanisms; the baffle comprises a front baffle, a rear baffle, a left baffle, and a right baffle; the support fabric is in contact with the breathable support plate; two ends of the support fabric are respectively wound around the left roller and the right roller; the left roller and the right roller are fixed to a frame; the left roller and the right roller are respectively connected to the roller power mechanisms; the roller power mechanisms are respectively configured to drive the left roller and the right roller to rotate; the left baffle and/or the right baffle are movable structures that are configured to be opened and closed; and when the left baffle and the right baffle are closed, the support fabric and the breathable support plate are tightly sealed.

5. The breeding and air drying system for the saprophagous insect according to claim 1, wherein a temperature and humidity sensor is provided at the air outlet.

6. The breeding and air drying system for the saprophagous insect according to claim 1, wherein the plurality of insect breeding layers further comprise a front, rear, left, and right portion, a support fabric or support mesh, a left roller, a right roller, and roller power mechanisms; the baffle comprises a front baffle, a rear baffle, a left baffle, and a right baffle; the support fabric is in contact with the breathable support plate; two ends of the support fabric are respectively wound around the left roller and the right roller; the left roller and the right roller are fixed to a frame; the left roller and the right roller are respectively connected to the roller power mechanisms; the roller power mechanisms are respectively configured to drive the left roller and the right roller to rotate; the left baffle and/or the right baffle are movable structures that are configured to be opened and closed; and when the left baffle and the right baffle are closed, the support fabric and the breathable support plate are tightly sealed.

7. The breeding and air drying system for the saprophagous insect according to claim 6, wherein the roller power mechanism comprises a linear guide rail, a guide rail motor, a roller motor, a driven gear provided at an end of the roller, and an driving gear provided at an end of the roller motor; the roller motor is fixed to a slider of the linear guide rail; and the guide rail motor drives the slider to move linearly.

8. The breeding and air drying system for the saprophagous insect according to claim 6, wherein the left baffle and/or the right baffle are fixed to the frame through a rotating shaft; and the rotating shaft is connected to a rotating shaft power mechanism.

9. A breeding and air drying method for a saprophagous insect, implemented by the breeding and air drying system for the saprophagous insect according to claim 1, and comprising the following steps:
(1) putting larvae of the saprophagous insect and a feed together on the plurality of insect breeding layers, and controlling a temperature, a humidity, and oxygen content required for breeding the saprophagous insect;
(2) when air drying is needed at an end of breeding: closing the breeding air inlet of the plurality of insect breeding layers that need air drying and the breeding air inlet of an adjacent insect breeding layer below, closing the air outlet of the adjacent insect breeding layer below, and opening the drying air inlet of the adjacent insect breeding layer below such that the dry hot air passes through the plurality of insect breeding layers that need air drying and flows out from the air outlet of the insect breeding layer that needs air drying, thereby achieving in-situ air drying of a residual feed and the larvae; and
(3) allowing, during air drying, the larvae to be heated and flip in the residual feed, wherein during air drying, mature larvae flip from a lower layer to an upper layer, playing a role in loosening, flipping, and stirring a material, thereby greatly improving an air drying efficiency.

10. The breeding and air drying method for the saprophagous insect according to claim 9, wherein step 2 uses an intermittent air drying method, comprising: air-drying for a period of time, pausing for a period of time, and repeating the air-drying and the pausing, wherein during air drying, mature larvae flip from a lower layer to an upper layer, while during pausing, the mature larvae flip from the upper layer to the lower layer; and repetition of the air-drying and the pausing, the material on the air-dried insect breeding layer is loosened and flipped, thereby improving breathability and the air drying efficiency.

11. The breeding and air drying method for the saprophagous insect according to claim 10, wherein the dry hot air is high-pressure dry hot air.

12. The breeding and air drying method for the saprophagous insect according to claim 9, wherein the dry hot air is high-pressure dry hot air.

13. The breeding and air drying method for the saprophagous insect according to claim 9, wherein the breeding and air drying system further comprises a control system; and the breeding air inlet valve and the hot air inlet valve are electric valves, and the breeding air inlet valve and the hot air inlet valve are connected to the control system, respectively.

14. The breeding and air drying method for the saprophagous insect according to claim 9, wherein a temperature and humidity sensor is provided at the air outlet.

15. The breeding and air drying method for the saprophagous insect according to claim 9, wherein the plurality of insect breeding layers further comprise a front, rear, left, and right portion, a support fabric or support mesh, a left roller, a right roller, and roller power mechanisms; the baffle comprises a front baffle, a rear baffle, a left baffle, and a right baffle; the support fabric is in contact with the breathable support plate; two ends of the support fabric are respectively wound around the left roller and the right roller; the left roller and the right roller are fixed to a frame; the left roller and the right roller are respectively connected to the roller power mechanisms; the roller power mechanisms are respectively configured to drive the left roller and the right roller to rotate; the left baffle and/or the right baffle are movable structures that are configured to be opened and closed; and when the left baffle and the right baffle are closed, the support fabric and the breathable support plate are tightly sealed.

16. The breeding and air drying method for the saprophagous insect according to claim 15, wherein the roller power mechanism comprises a linear guide rail, a guide rail motor, a roller motor, a driven gear provided at an end of the roller, and an driving gear provided at an end of the roller motor; the roller motor is fixed to a slider of the linear guide rail; and the guide rail motor drives the slider to move linearly.

17. The breeding and air drying method for the saprophagous insect according to claim 15, wherein the left baffle and/or the right baffle are fixed to the frame through a rotating shaft; and the rotating shaft is connected to a rotating shaft power mechanism.

* * * * *